US005658247A

United States Patent [19]
Henley

[11] Patent Number: 5,658,247
[45] Date of Patent: *Aug. 19, 1997

[54] IONOSONIC DRUG DELIVERY APPARATUS

[76] Inventor: Julian L. Henley, 38 Munger Rd., Guilford, Conn. 06437

[*] Notice: The term of this patent shall not extend beyond the expiration date of Pat. No. 5,160,316.

[21] Appl. No.: 470,946

[22] Filed: Jun. 6, 1995

Related U.S. Application Data

[62] Division of Ser. No. 316,817, Oct. 3, 1994, which is a continuation of Ser. No. 44,586, Apr. 7, 1993, abandoned.

[51] Int. Cl.$^6$ ................................................. A61N 1/30
[52] U.S. Cl. ................................................. 604/20
[58] Field of Search .................... 604/20, 22; 607/97, 607/115, 120, 149, 152; 601/1

[56] References Cited

U.S. PATENT DOCUMENTS

| | | | |
|---|---|---|---|
| 4,211,222 | 7/1980 | Tapper | 604/20 |
| 4,474,570 | 10/1984 | Ariura et al. | |
| 4,708,716 | 11/1987 | Sibalis | 604/20 |
| 4,764,164 | 8/1988 | Sasaki | 604/20 |
| 4,950,229 | 8/1990 | Sage, Jr. | 604/20 |
| 5,115,805 | 5/1992 | Bommannan et al. | 601/1 |
| 5,160,316 | 11/1992 | Henley | |
| 5,415,629 | 5/1995 | Henley | |

FOREIGN PATENT DOCUMENTS

| | | | |
|---|---|---|---|
| 0931191 | 5/1982 | U.S.S.R. | 604/20 |
| 1003853 | 3/1983 | U.S.S.R. | 604/20 |

*Primary Examiner*—Mark Bockelman
*Attorney, Agent, or Firm*—Michael G. Petit

[57] ABSTRACT

An improved apparatus for the iontophoretic-ultrasonic (ionosonic) transdermal delivery of medication across the skin or other biological membrane so the medication can be absorbed by the adjacent tissues and blood vessels. The apparatus can be adapted for large dermal area application or for a smaller area of application, depending on the choice of specific electrode employed. The apparatus comprises a multichannel iontophoretic applicator electrode. Multiple piezoelectric elements are mounted on the ionotophoetic electrode. The combination of ultrasonic vibration and iontophoresis creates a significant improvement in the penetration of medicament in contact with the skin or mucous membrane underlying the electrode. Drug delivery systems employing biofeedback such as the transcutaneous delivery of insulin based on tissue glucose are outlined based on this ionosonic technology.

3 Claims, 1 Drawing Sheet

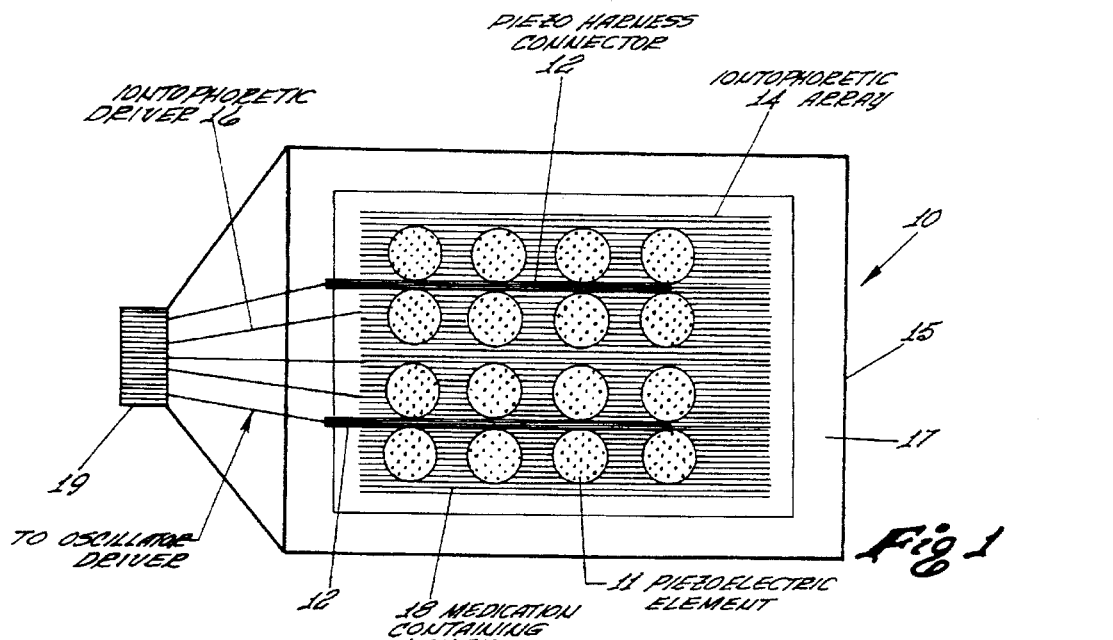
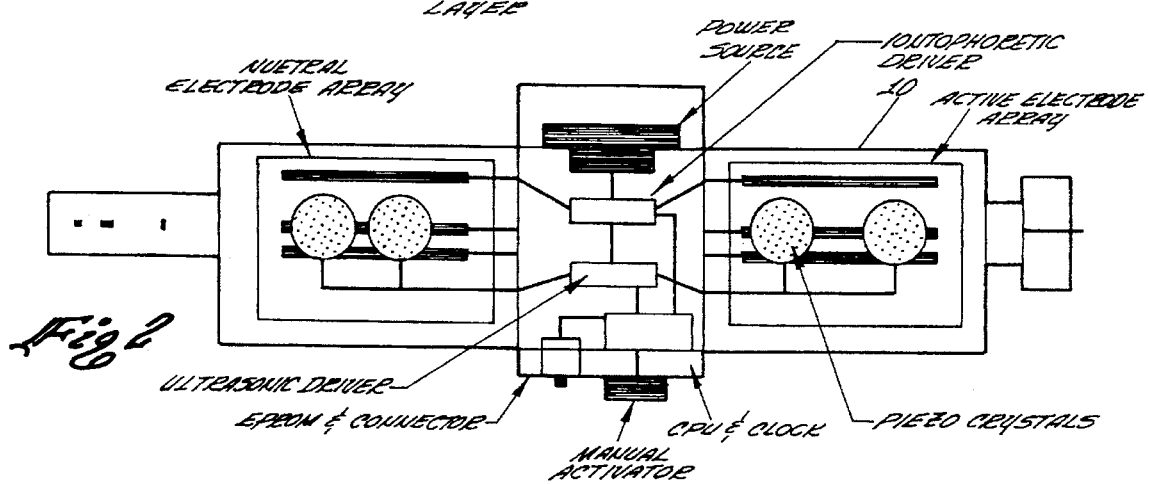
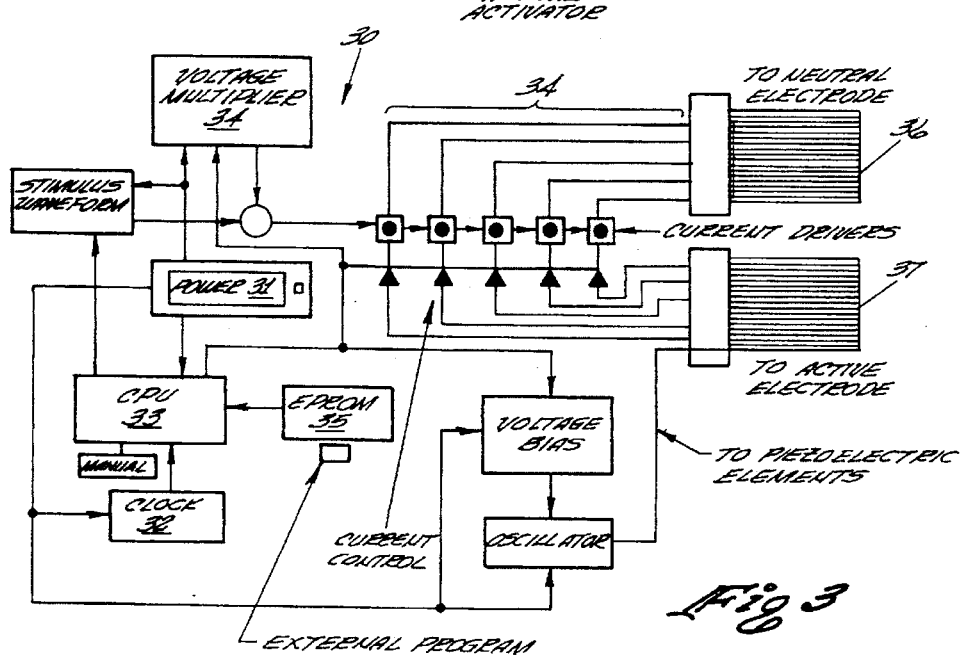

IONOSONIC DRUG DELIVERY APPARATUS

REFERENCE TO RELATED APPLICATIONS

This application is a Divisional of U.S. patent application Ser. No. 08/316,817, filed Oct. 3, 1994 now pending which is a continuation of application Ser. No. 08/044,586 filed Apr. 7, 1993, now abandoned.

BACKGROUND OF THE INVENTION

1. Field of the Invention

This invention relates generally to the transdermal delivery of medicament and, more specifically, to an apparatus for the iontophoretic and ultrasonic delivery of medication across the skin or other biological tissue.

2. Prior Art

Iontophoresis has existed for several centuries as a means for applying medication locally through a patient's skin and for delivering medicaments to the eyes and ears. The application of an electric field to the skin is known to greatly enhance the skin's permeability to various ionic agents. The use of iontophoretic techniques has obviated the need for hypodermic injection of certain medicaments, thereby eliminating the concomitant problems of trauma, pain and risk of infection to the patient.

Iontophoresis involves the application of an electromotive force to drive or repel oppositely charged ions through the dermal layers into the area to be treated; either into the surrounding tissues for localized treatment or into the circulatory system for systemic treatment. Positively charged ions are driven into the skin at the anode while negatively charged ions are driven into the skin at the cathode. Studies have shown increased skin penetration of drugs at anodic or cathodic electrodes regardless of the predominant molecular ionic charge. This effect is mediated by polarization and osmotic effects. Regardless of the electrical charge on the medicament employed, two electrodes are used in conjunction with the patient's skin to form a closed circuit to promote the penetration or absorption of the medicament through the skin underlying the working electrode.

One readily observed benefit of transdermal iontophoretic drug delivery is the increased efficacy of the drugs delivered in this fashion. U.S. Pat. No. 5,160,316, to the instant inventor, incorporated herein by reference, describes the use of a multichannel dispersive eleotrode. Each channel is driven by separate electronic circuits to assure wide dispersion and enhanced penetration of medicament. Such wide field electrodes not only can cover a wide area of body without succumbing to "tunneling effects" but provide sufficient skin penetration to function as a systemic drug delivery system. A co-pending patent application by the present inventor describes a user-friendly iontophoretic system to deliver nicotine as a device to help people quit smoking or, alternatively, to provide established smokers with a noncarcinogenic smokeless cigarette.

Prior art iontophoretic systems have not proved useful for delivery of insulin via the transdermal route. Such a system would be extremely important in the management of diabetic patients and in decreasing the long term complications of diabetes. The patient would be freed from multiple injections of insulin and strict dietary controls which are the mainstay of current therapy of Diabetes Mellitus. It is believed that improved control of intraday glucose fluctuations will significantly decrease the long term complications of diabetes such as blindness and renal failure. Improved control of diabetic pregnancy and children will enhance and prolong life. An iontophoretic insulin delivery system must employ an electrode that avoids current flowing along the path of least resistance into a lesion or skin rupture, resulting in a localized burn.

The foregoing problems are solved by the present invention by providing an improved iontophoretic medicament applicator and combining this iontophoretic dispersion electrode with ultrasonic enhancement of penetration. Ultrasonic fields can readily be generated in the skin underlying an electrode by means of oscillator circuits applying a high frequency voltage waveform to piezoelectric crystals (i.e. quartz) mounted on the dispersive application electrode. It is the nature of piezoelectric crystals to convert electrical oscillations to vibration by means of crystal lattice elongation. Numerous materials such as ceramics (barium titanate), and variations of lead zicornate-lead titanate exhibit good piezoelectric properties and can be mounted on such an electrode. A preferred manufacture of a pliant contouring electrode producing low energy ultrasonic fields utilizes a sheet of Kynar™ polyvinelidene fluoride film that exhibits piezoelectric properties when energized yet retains pliability, stability and absence of toxicity. Such laminates of piezo film are known in the art and have already been manufactured. A bending motion (analogous to bimetallic action of thermostats) can be generated in response to an applied voltage where the top film expands while the bottom contracts. Alternating voltage creates film vibration in phase with applied oscillator output. For higher energy applications multiple mounted piezoelectric crystals or ceramic elements on a flexible iontophoretic sheet will be preferable.

SUMMARY OF THE INVENTION

Surprisingly, the instant inventor has discovered that combining a multichannel iontophoretic electrode with ultrasonic enhancement greatly improves transdermal penetration of larger molecules such as insulin or other peptide. Ultrasound applied to the skin has been shown to enhance skin penetration by (a) disrupting the protective keratin layer; and (b) forming micro-droplets that can readily be charged. A transdermal delivery system combining ultrasound and iontophoresis may be adapted to incerporate percutaneous infrared based glucose sensor technology with the ultrasonic-iontophoretic driver electrode in a biofeedback configuration. Such a system can be worn by a suffering diabetic. The sensor monitors the tissue glucose level, and if it exceeds a specified level the unit will begin to drive insulin through the skin until a normal glucose level is reestablished.

The improved iontophoretic applicator may also be suitable for treatment of large areas of skin where the ultrasonic component of the medicament driver electrode will further enhance the penetration of substances like antibiotic, antifungal, or growth factors when driven into a burn eschar to promote healing and minimize infection.

It is, therefore, a primary object of this invention to describe the construction of a driver electrode that combines the multichannel iontophoretic electrode with piezoelectric ultrasonic application elements into a combined structure which when linked with electrophoretic and ultrasonic driver circuits create a system for greatly enhanced skin penetration of medications, hormones, peptide and other therapeutic substances.

It is an additional object of the present invention to provide an improved iontophoretic medicament applicator that can be used to treat a large dermal area.

It is another object of the present invention to provide a more efficient iontophoretic medicament applicator by coupling the iontophoretic applicator electrode with piezoelectric ultrasonic elements at the site of iontophoretic application.

It is still another object of the present invention to provide an improved iontophoretic medicament applicator that is driven by reusable circuit and ultrasonic sources and comprises a disposable skin contacting surface that contains an iontophoretic dispersion electrode open cell medicament reservoir in contact with the skin surface.

It is a feature of the present invention that the iontophoretic medicament applicator for large dermal areas employs a multichannel electrodispersive matrix to drive the ionic medicament from the matrix or pad into the skin area.

It is another feature of the present invention that the iontophoretic medicament applicator for large dermal areas employs a carrier matrix with the medicament dispersed therewithin in combination with an adhesive layer to facilitate fastening to the patient's skin.

It is a further feature of the present invention that the iontophoretic medicament applicator for large dermal areas employs a conductive matrix and a carrier matrix with the medicament dispersed therewithin and which are sufficiently flexible to conform to the contours of the body area being treated.

It is still another object of the present invention to provide a disposable iontophoretic medicament applicator which employs an absorbent, inert material that is non-corrosive to contain the medicament or therapeutic agent.

It is yet another feature of the present invention that the disposable iontophoretic medicament applicator and the neutral electrode array and active electrode array are integrated into a single band type device to be worn about an extremity providing for comfort and electrical contact with skin. The ultrasonic crystal sources are preferably within close proximity to the dispersive iontophoretic electrodes while the power source and control circuitry for the ultrasonic drivers and the current limited drivers for the iontophoretic components are mounted on a band-type device as a control structure similar to that of a large watch.

It is yet another feature of the present invention that it provide a needleless transcutaneous drug delivery system in which the multichannel iontophoretic dispersion electrode together with the ultrasonic elements can comprise a flexible sheet with remote power and control circuits joined to the flexible sheet by ribbon cabling for treatments requiring higher power densities, higher dosing or treatment of specific areas such as burns, infection or special anatomic areas such as oral gums.

It is yet another object of this invention to describe a system for which overcomes biological boundaries against diffusion by means of the synergistic combination of multichannel iontophoresis and ultrasonic enhancement.

It is another object of the invention to provide a system for painless, controlled and safe delivery of drugs, peptide and other substances through the skin or mucous membrane.

It is an advantage of the present invention that the iontophoretic medicament applicator for large dermal areas improves the efficacy of topical agents and reduces the risk of harmful side effects that may occur with oral systemic treatment techniques.

It is another advantage of the present invention that the disposable iontophoretic medicament applicator for difficult to treat areas conducts the electrical current to the tissue through the solution into which the medicament is dissolved.

It is still another advantage of the present invention that the improved disposable iontophoretic medicament applicator has a low production cost, is safe to use and increases the efficacy of the medicament employed.

It is another feature of this invention that this wide area iontophoretic electrode is further enhanced by the adhesion of multiple ultrasonic elements corresponding to each dispersion electrode channel to further enhance the applied and iontophoretically driven medicament.

It is still another feature of this combined system that the array of ultrasonic elements each generating (30 khz–60 khz) may be driven and energized by circuitry in either serially, in parallel, or a combination of each, or even in multiplex fashion depending on energy sources and level of miniaturization and portability.

It is still another feature that the ultrasonic field in lower energy applications can be generated by incorporating a commercially available piezo film (i.e. Kynar PVDF film).

A preferred embodiment may be worn like a wide watch band with the electronics and power source will be mounted thereon in a manner similar to a large watch. The inner surface of this band will contain the active and grounding multichannel dispersive electrode. The ultrasonic elements are to be placed within this band in close proximity to each electrode channel. The inner surface may be an adhesive, an open cell material, insulin or other peptide-impregnated hydrogel or other similar matrix. This inner band surface containing the medicament will be disposable and contain a specified amount of desired medicament.

These and other objects, features and advantages are obtained by the improved iontophoretic medicament applicator of the present invention. Various embodiments of the invention can be used to treat large dermal areas, localized areas or small and difficult to reach areas, and even include a "watch band" type of a systemic drug delivery system.

This system readily lends itself to systemic delivery of medication under the control of a physiological sensor connected to the delivery system in a biofeedback configuration. Delivery of nitroglycerin based on heart rate sensing; delivery of blood pressure medication based on blood pressure sensing; and ultimately, the transdermal delivery of insulin by means of the iontophoretic-ultrasonic system regulated and controlled by a similarly noninvasive glucose sensor.

BRIEF DESCRIPTION OF THE DRAWINGS

The objects, features and advantages of the invention will become apparent upon consideration of the following detailed disclosure of the invention, especially when it is taken in conjunction with the accompanying drawings wherein:

FIG. 1 is a top plan view of one embodiment of the improved multichannel iontophoretic applicator combined with several of the plurality of ultrasonic elements which can be used to treat large dermal areas.

FIG. 2 is a top, somewhat schematic, plan view of a miniaturized embodiment of the improved iontophoretic-ultrasonic delivery system combined with a sensor (e.g.; tissue glucose, blood pressure, or heart rate sensors) to form a biofeedback system for intelligent and controlled drug delivery. This system can be worn as a "watch band" on an extremity.

FIG. 3 is a block circuit diagram of the iontophoretic-ultrasonic (ionosonic) medicament applicator's electrical control circuit used in conjunction with above applicators either as a separate power and control unit or integrated into a single unit if market demand justifies the costs of such miniaturization.

DETAILED DESCRIPTION OF THE PREFERRED EMBODIMENT

An ionosonic applicator, generally indicated at the numeral 10, is shown in FIG. 1. The applicator 10 includes a working electrode 14 which forms a closed circuit through the patient's body when current passes therethrough which promotes the penetration or absorption of an ionic medicament contained in a layer 18 adjacent to and in electrical communication with the working electrode 14. The polarity of the working electrode 10 is selected based upon the polarity of the medicament to be administered. The electrode 14 preferably comprises a flexible sheet or film forming a conductive matrix 15 having a current distributing conductive layer, such as a metallic foil, a conductive rubber or resin film, carbon film or other conductive coating or electro-dispersive material. The conductive matrix 15 is flexible so that it may be contoured to the body area on which it is placed and still cover a relatively wide area. Matrix 15 has a medicament carrying layer 18 attached to it, such as by an adhesive. The medicament carrying layer 18 is preferably formed from a porous material about ¼ of an inch thick which can be a honeycombed sponge-like material with vertical cells to minimize cross flow or lateral dispersion of the medicament. The grounding electrode (not shown) employed with the multichannel electrode 14 must also cover an area of skin which is similar in size to the area covered by electrode 14.

A ribbon connector (not shown) connects an electrical power source (not shown) to the multichannel electrode 14 and delivers the electrical current by means of the multi-connectors 19 to the lead wires 16 that form the individual electrically conductive channels in the conductive matrix 15. Since the material of construction is flexible, the electrode 10 may be folded over a rigid supporting substrate above the connectors 19 to insure that a good electrical connection is made with the ribbon connector. Each channel in the iontophoretic array 14 preferably carries no more than 1 milliamps. The amount of current that flows to each channel is controlled by the control circuit (shown in FIG. 3) to prevent a tunneling effect from occurring. This prevents the flow of current along the path of least resistance through a lesion or skin rupture, for example, resulting in a burn to the patient at that location. The multichannel electrode 14 can employ a circuit pattern etched such as by laser or photoetching onto, for example, a metal coated Mylar® plastic sheet with each channel isolated to facilitate dispersion over a broad surface area.

Each channel formed by the lead wires 16 can be electrically driven simultaneously or in a sequential multiplex fashion. The use of simultaneous or parallel electrical current to each lead wire 16 in the array 14 would be employed, for example, in the application of medicament to burns where a wide area of dispersion is required. The iontosonic applicator greatly improves the skin penetration by the medicament to actively deliver the medicament to either a wide regional area or to a specific lesion.

Ultrasonic elements 11 made of piezoelectric crystal elements are mounted on this flexible electrode by means of a suitable adhesive such as Silastic™ brand of silicone adhesive. Driving oscillator connections 12 to the crystals can be photoetched onto a polymer sheet (e.g.; metalized Mylar™) with perforations on the sheet which facilitate mounting of the ultrasonic elements. This electrode can be effective in moving Insulin across skin, as well as antibiotics, antifungal, anti-inflammatory, blood pressure medication and cardiotropic drugs; either as direct drive, logic control timer drive or more elegantly as biofeedback control configuration. It is also effective in the treatment of wide field dermatological conditions, such as eczema, psoriasis and acne. It is also effective for ionic retention of skin hydrating media to facilitate skin hydration in cosmetic applications and in dermal exfoliation to drive medication into the skin in order to inflame the skin and cause the peeling of the external skin layer to stimulate reformation of collagen and collagen growth factors. The ionosonic applicator may also prove useful for driving Minoxidil™ or related compounds into the scalp to enhance hair growth and/or ameliorate baldness. The construction of ultrasonic elements can be piezo-electric crystals, ceramics or distributed segments of Kynar™ PVDF piezo film.

The open-celled sponge-like material in the medicament carrying layer 18 should be inert to the medicament or treatment agent being employed, as well as being noncorrosive and stable. Suitable materials include plastic pads, such as polyethylene, paper or cotton, porous ceramics, open-celled porous polytetrafluoro ethylene, other inert plastics, and open-celled silicone rubber, preferably with vertically aligned medicament-containing cells or tubes.

FIG. 3 shows a block circuit diagram of the iontophoretic medicator electrical control circuit suitable for use with the ionosonic applicator of FIG. 1 and the miniaturized ionosonic applicator diagrammed in FIG. 2. The control circuit, generally indicated at 30, may be either integrated with the application, as shown in FIG. 2, or boxed separately and including connection means adapted to electrically connect to the applicator to provide power to drive the applicator as shown in FIG. 1. The control circuit is equipped with a power source 31 which may be either a battery or an isolated wall source.

The control box 30 is provided with a clock-operated timer switch 32 to preset the length of iontophoretic treatment mediated by the integral CPU. Once the length of time has been selected, a voltage multiplier is utilized to provide the current to iontophoretically drive the medicament into the patient's skin. The current is set and administered until the end of the treatment period. When the clock 32 signals the end of the treatment period, the electrical current to the electrode 10 is gradually terminated by a ramping down of the current to the patient to avoid abrupt change. Ribbon cable (not shown) provides a flexible connection to the multichannel neutral and active electrodes as indicated in FIG. 3, as well as delivering oscillator power for the piezoelectric crystals 11 mounted on the applicator electrode 10. Internal circuit board controls allow for frequency adjustment, adjustment of maximum current per iontophoretic channel (not to exceed 0.6 to 1.2 ma range),and internal control that will shut down any iontophoretic channel electrically performing outside a "normal" range of encountered biological impedance.

FIG. 3 shows the block circuit diagram of the large area iontophoretic medicator control circuit employed with the multichannel iontophoretic applicator of FIG. 2. An isolated current loop generator is employed to feed current to the individual channels in the multichannel electrode via the plurality of individual current loops. Each current loop drives one band or channel in the multichannel electrode. It has been found that 0.6 milliamps current flowing to each channel used within a wide field dispersion grounding electrode, such as that shown in FIG. 1, provides a safe level for operating the iontophoretic device. This level of current avoids the tunnelling effect of current flowing along the path of least resistance and concentrating in, for example, a lesion or skin rupture, resulting in a burn to the patient. This permits current to be distributed over the large area of the multichannel electrode to drive medicament through a patient's skin over a large dermal area. Depending upon the electrode configuration, this current level can vary from about 0.1 to about 1.2 milliamps. The novel introduction of distributed ultrasonic piezoelectric elements combined with the iontophoretic multi electrodes described above greatly enhances the rate of penetration of many molecules. The use of ionosonic applications to administer insulin transdermally now becomes feasible.

While the invention has been described above with references to specific embodiments thereof, it is apparent that many changes, modifications and variations in the materials, arrangements of parts and steps can be made without departing from the inventive concept disclosed herein. For example, in employing the multichannel iontophoretic electrode of the present invention, it is possible to employ a biofeedback control of its operation to disperse, for example, more cardiovascular medication during periods of increased physiological demands, such as during exercise or an angina attack, by linking the penetration of nitroglycerine with heart rate; the physiological indicator of oxygen demand by the heart. In the latter instance, a sensor electrode would measure the increased demand and signal the controller 30 to stimulate more delivery of the transdermal medication, in this case, nitroglycerine (commercially available under the trade name Nitropaste). This type of a biofeedback coupled with ionosonic application provides an active system for percutaneous nitroglycerine delivery which is an improvement over existing passive percutaneous delivery systems. The present invention creates a further improvement in transdermal penetration of medicament over prior purely iontophoretic delivery system by introducing ultrasonic drivers at the site of iontophoretic penetration.

Alternate applications also exist in hormonal therapy, for example in the administration of insulin or steroids based on blood sugar levels and diurnal cycles, as appropriate. The large area multichannel electrode shown in FIG. 1 can also be adapted for use in dental anaesthesia in the form of a bite block, burn treatment and for the treatment of baldness, such as by the transdermal administration of Minoxidil®. Additionally, a conductive gel can also be used to impregnate the porous medicament carrying medium to increase the physical stability and the tissue adhering characteristics of the electrode. Or, a medicament may be dispersed in conductive gel and a layer of the gel serve as the medicament carrying layer.

Accordingly, the spirit and broad scope of the appended claims is intended to embrace all such changes, modifications and variations that may occur to one of skill in the art upon a reading of the disclosure. All patent applications, patents and other publications cited herein are incorporated by reference in their entirety.

I claim:

1. An iontophoretic transdermal drug delivery device adapted to releasably attach to a person's body so that a skin-contacting surface of said device is adjacent to a portion of the person's skin, said device having electrical connection means thereon adapted to electrically connect said device to a multiplicity of current sources, said device being operable for iontophoretically driving a medicament across said skin-contacting surface of said device into said portion of the person's skin, said device further comprising, in combination:

(a) a medicament carrying layer in fluid communication with said skin-contacting surface of said device comprising a porous sheet impregnated with a medicament containing fluid;

(b) an iontophoresis electrode in electrical communication with said medicament carrying layer providing means for iontophoretically driving said medicament into the person's skin, said iontophoresis electrode further comprising a plurality of electrode channels, each electrode channel of said plurality of electrode channels being electrically isolated from other electrode channels comprising said plurality electrode channels, said plurality of electrode channels having electrical connection means connected thereto adapted for simultaneous electrical connection of selected electrode channels to the same or different current sources, said each electrode channel being in electrical communication with said medicament carrying layer; and (c) a plurality of piezoelectric elements affixed to a flexible plastic sheet affixed to and overlying said iontophoresis electrode.

2. The device of claim 1 wherein said plurality of electrically isolated electrode channels comprising said iontophoresis electrode consists of a plurality of electrically isolated electrically conductive traces affixed to a surface of a flexible sheet of electrically non-conductive material, each trace of said plurality of electrically isolated electrical conductive traces having electrical connection means adapted for electrically connecting said each trace to a current source.

3. An iontophoretic transdermal drug delivery device adapted to releasably attach to a person's body so that a skin-contacting surface of said device is adjacent to a portion of the person's skin, said device having electrical connection means thereon adapted to electrically connect said device to a multiplicity of current sources, said device being operable for iontophoretically driving a medicament across said skin-contacting surface of said device into said portion of the person's skin, said device further comprising, in combination:

(a) a medicament carrying layer in fluid communication with said skin-contacting surface of said device comprising a porous sheet impregnated with a medicament containing fluid;

(b) an iontophoresis electrode in electrical communication with said medicament carrying layer providing means for iontophoretically driving said medicament into the person's skin, said iontophoresis electrode further comprising at least three electrode channels, each electrode channel of said at least three electrode channels being electrically isolated from other electrode channels, said at least three electrode channels having electrical connection means connected thereto adapted for simultaneous electrical connection of selected electrode channels to the same or different current sources, said each electrode channel being in electrical communication with said medicament carrying layer, and wherein said at least three electrically isolated electrode channels consists of a at least three electrically isolated electrically conductive traces affixed to a surface of a flexible sheet of electrically non-conductive material.

\* \* \* \* \*